(12) United States Patent
Bouttenot

(10) Patent No.: US 12,370,095 B2
(45) Date of Patent: Jul. 29, 2025

(54) FECAL INCONTINENCE LEAK PREVENTION UNDERGARMENT

(71) Applicant: Marc Bouttenot, Fairfield, IA (US)

(72) Inventor: Marc Bouttenot, Fairfield, IA (US)

( * ) Notice: Subject to any disclaimer, the term of this patent is extended or adjusted under 35 U.S.C. 154(b) by 0 days.

(21) Appl. No.: 18/648,690

(22) Filed: Apr. 29, 2024

(65) Prior Publication Data
US 2025/0134733 A1   May 1, 2025

Related U.S. Application Data

(60) Provisional application No. 63/594,582, filed on Oct. 31, 2023.

(51) Int. Cl.
*A61F 13/494*   (2006.01)
*A41B 9/00*   (2006.01)

(52) U.S. Cl.
CPC .......... *A61F 13/4946* (2013.01); *A41B 9/001* (2013.01)

(58) Field of Classification Search
CPC ......... A41B 9/00; A41B 9/001; A61F 13/496; A61F 13/4963; A61F 13/4946
USPC ............................................................ 2/400
See application file for complete search history.

(56) References Cited

U.S. PATENT DOCUMENTS

| | | | |
|---|---|---|---|
| 3,489,149 A * | 1/1970 | Larson .................. | A61F 13/72 604/397 |
| 3,608,551 A * | 9/1971 | Seijo .................... | A61F 13/72 604/397 |
| 4,646,362 A * | 3/1987 | Heran ................ | A61F 13/49017 2/403 |
| 5,546,607 A * | 8/1996 | Roberts ................. | A61F 13/505 2/400 |
| 6,061,839 A * | 5/2000 | Smolik ................. | A61F 13/471 2/403 |
| 6,648,865 B1 | 11/2003 | Stiehl | |
| 7,150,731 B2 | 12/2006 | Cazzato | |
| 7,195,619 B2 | 3/2007 | Manasek | |
| 7,763,002 B2 | 7/2010 | Otsubo | |
| 8,870,840 B2 | 10/2014 | Close | |
| 10,750,793 B1 * | 8/2020 | Theodoridis ........... | A41B 9/001 |
| 12,150,494 B2 * | 11/2024 | Towns-Scott .......... | A41D 27/20 |
| 2007/0255245 A1 * | 11/2007 | Asp ........................ | A61F 13/496 604/385.24 |
| 2011/0224639 A1 * | 9/2011 | Venable ................ | A61F 13/496 604/385.01 |

(Continued)

*Primary Examiner* — Jocelyn Bravo
(74) *Attorney, Agent, or Firm* — Brennan, Manna & Diamond, LLC

(57) ABSTRACT

An improved fecal incontinence leak prevention underwear or undergarment designed to address the challenges faced by individuals with fecal incontinence, including the risk of leaks and stains on clothing is described. The rear surface of the underwear or undergarment has a multi-layered rear surface adapted to cover a buttock region of the wearer. The multi-layered portion is strategically designed to extend from the crotch region to the cleft of a wearer. The multi-layered portion comprises an innermost layer made from moisture-resistant fabric, a middle layer of absorbent terry-cloth material, and an outer layer consistent with standard underwear or undergarment materials, typically cotton (i.e., fabric). In one embodiment, the multi-layered portion has varied density to accommodate different levels of protection and comfort.

16 Claims, 4 Drawing Sheets

(56) References Cited

U.S. PATENT DOCUMENTS

| | | | |
|---|---|---|---|
| 2014/0039432 A1* | 2/2014 | Dunbar | A61F 13/15577 |
| | | | 604/394 |
| 2015/0290049 A1* | 10/2015 | Riha-Scott | A41B 9/001 |
| | | | 604/387 |
| 2018/0085263 A1* | 3/2018 | Boll | A61F 13/53 |
| 2020/0390162 A1* | 12/2020 | Ishihara | A61F 13/15 |
| 2023/0051090 A1* | 2/2023 | Husmark | A61L 15/46 |
| 2023/0338206 A1* | 10/2023 | Welch | A41D 31/102 |
| 2024/0050288 A1* | 2/2024 | Basius | A61F 13/49426 |
| 2024/0398634 A1* | 12/2024 | Power | A61F 13/15268 |

* cited by examiner

FECAL INCONTINENCE LEAK PREVENTION UNDERGARMENT

CROSS-REFERENCE TO RELATED APPLICATION

The present application claims priority to, and the benefit of, U.S. Provisional Application No. 63/594,582, which was filed on Oct. 31, 2023, and is incorporated herein by reference in its entirety.

FIELD OF THE INVENTION

The present invention generally relates to the field of underwear, undergarments, and fecal continence absorbent devices. More specifically, the present invention relates to a novel underwear or undergarment designed to absorb fecal incontinence leaks to prevent stains and leaks on clothing. The underwear or undergarment includes a multi-layered anal region cover which has three layers. The multi-layered anal region cover has an innermost layer made from moisture-resistant fabric, a middle layer of absorbent terrycloth material, and an outer layer consistent with standard underwear or undergarment materials, typically cotton (i.e., fabric). The combination of layers forms a pad-like structure that offers comprehensive protection against leaks and contributes to the longevity of the underwear or undergarment by withstanding significant wear and tear. Accordingly, the present disclosure makes specific reference thereto. Nonetheless, it is to be appreciated that aspects of the present invention are also equally applicable to other like applications, devices, and methods of manufacture.

BACKGROUND

By way of background, fecal incontinence is a condition characterized by the inability to control bowel movements, leading to unexpected leakage of stool from the rectum. Fecal incontinence affects a significant number of individuals and can stem from multiple causes, including, but not limited to, muscle or nerve damage which may be related to aging or childbirth, chronic diseases like diabetes, digestive disorders such as Crohn's disease, or irritable bowel syndrome, and severe constipation leading to overflow incontinence. Fecal incontinence leaks can stain clothing and produce a foul odor leading to physical and psychological discomfort to individuals.

Many people resort to the use of adult diapers for managing such leaks to protect clothing and minimize accidents. However, despite the practicality of adult diapers, many individuals find wearing adult diapers unappealing and embarrassing. This also can deter people from using adult diapers, even when diapers offer a practical solution to manage incontinence. Adult diapers can also be bulky and uncomfortable, making them less desirable for daily wear. Size and the noise of adult diapers, combined with the need for discreet disposal, add to the inconvenience and potential embarrassment for users. People desire an innovative and alternative solution to traditional adult diapers to manage the condition of fecal incontinence leaks.

Therefore, there exists a long-felt need in the art for an improved solution to maintain fecal incontinence leaks. There is also a long-felt need in the art for an improved underwear or undergarment that has a plurality of layers on the rear side to prevent fecal incontinence leaks. Additionally, there is a long-felt need in the art for a novel underwear or undergarment for men, women, and children that can replace conventional diapers for preventing stains and foul odor caused due to fecal incontinence leaks. Moreover, there is a long-felt need in the art for a novel fecal incontinence brief that helps reduce the stains from fecal incontinence seep through the brief onto clothing. Further, there is a long-felt need in the art of specially designed underwear or undergarment that eliminates the use of wearing adult diapers and includes three sewn layers to cover the buttocks to prevent fecal incontinence leaks. Furthermore, there is a long-felt need in the art for a novel underwear or undergarment that has extended life and is easy to wear. Finally, there is a long-felt need in the art for a fecal incontinence underwear or undergarment that has three layers sewn together on the rear side to form a pad-like structure to absorb fecal incontinence leaks.

The subject matter disclosed and claimed herein, in one embodiment thereof, comprises a fecal incontinence leak prevention underwear or undergarment. The underwear or undergarment includes a front surface, a rear surface adapted to cover the buttock region of a wearer, a multi-layered portion disposed on the rear surface, the multi-layered portion extends from a crotch region along a seam of the rear surface of leg openings. The multi-layered portion is adapted to cover the anal region up to the cleft of a wearer, thereby providing effective absorption of incontinence leakage. The multi-layered portion is made of three layers sewn to the rear surface and is flexible. The innermost layer is made from a moisture-resistant fabric, a middle layer is made up of an absorbent material, and an outer layer is made of a material used for making the underwear or undergarment.

In this manner, the fecal incontinence leak prevention underwear or undergarment of the present invention accomplishes all of the foregoing objectives and provides users with an undergarment that can be designed for men, women, and children and is reinforced with three layers to prevent fecal incontinence leaks. The underwear or undergarment helps reduce the chance any stains or leaks from fecal incontinence seep through undergarments. The multiple layers cover the anal region to absorb fecal leaks and extend the life of the underwear or undergarment. The underwear or undergarment eliminates the use of adult diapers and pads and is flexible. The layers are sewn thereby provide an effective absorption without any unintentional disengagement or sliding when worn.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a fecal incontinence leak prevention underwear or undergarment. The underwear or undergarment includes a front surface, a rear surface adapted to cover the buttock region of a wearer, a multi-layered portion disposed on the rear surface, the multi-layered portion extends from a crotch region along a seam of the rear surface of leg openings. The multi-layered portion is adapted to cover the anal region up to the cleft of a wearer, thereby providing effective absorption of incontinence leakage. The multi-layered portion is made of three layers sewn to the rear surface and is flexible.

In another aspect, a fecal incontinence leak prevention underwear or undergarment is disclosed. The underwear or undergarment includes a rear surface adapted to cover the buttock region of a wearer, wherein the rear surface has a multi-layered portion disposed thereon which extends from a crotch region along a seam of the rear surface of leg openings. The multi-layered portion includes an innermost layer made from a moisture-resistant fabric to prevent moisture leakage and staining outer clothing, a middle layer made up of an absorbent material, such as terrycloth, for absorbing moisture away from the skin and adding comfort, and an outer layer made of a material consistent with the material used for manufacturing standard underwear or undergarment.

In yet another embodiment, the multi-layered anal region cover extends from a crotch region along a seam of the rear surface of leg openings. The multi-layered anal region cover has a first side that extends away from a first leg opening of the underwear or undergarment and a second side that extends away from a second leg opening of the underwear or undergarment, the first side and the second side at a common point to form a closed structure of the multi-layered anal region cover.

In a further embodiment, the thickness of the multi-layered portion is about three to five times the thickness of the material of the standard underwear or undergarment and the design and shape of the multi-layered portion can be adjusted based on the design requirements of the underwear or undergarment.

In yet another aspect of the present invention, an anal incontinence leak prevention underwear or undergarment is disclosed. The underwear or undergarment includes a rear surface, the rear surface has a multi-layered portion disposed thereon which extends from a crotch region along a seam of the rear surface of leg openings to cover the anal region of a wearer of the underwear or undergarment. The multi-layered portion includes an innermost layer made from a moisture-resistant fabric, a middle layer made up of an absorbent material, and an outer layer made of a material consistent with the material used for manufacturing standard underwear or undergarment. The multi-layered portion is adapted to absorb incontinence leaks for more than 6 hours without leakage. The multi-layered portion can have different densities for offering graded protection and comfort.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
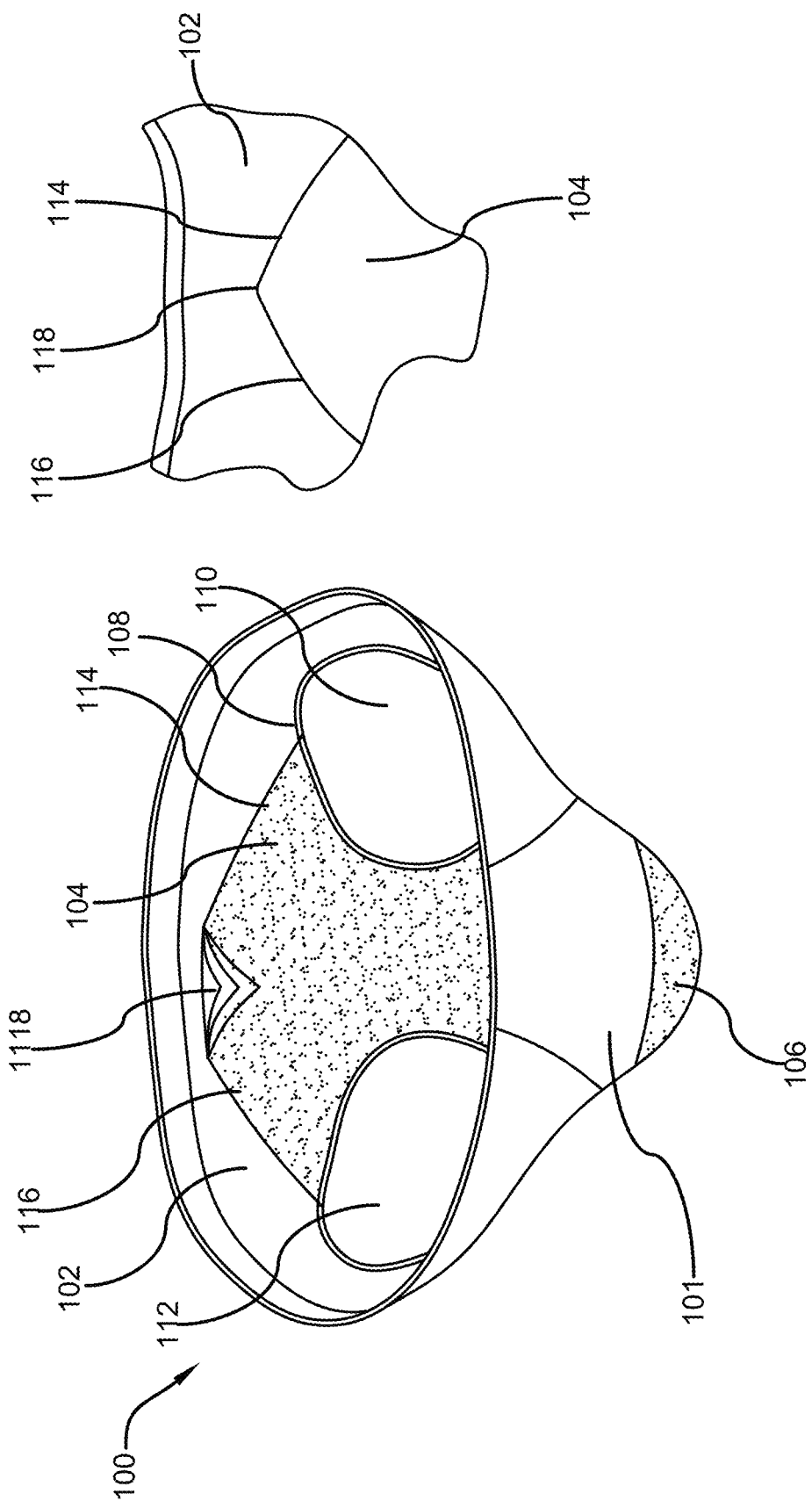
FIG. 1 illustrates a perspective view of the fecal incontinence leak prevention underwear or undergarment in accordance with one embodiment of the present invention.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an improved solution to maintain fecal incontinence leaks. There is also a long-felt need in the art for an improved underwear or undergarment that has a plurality of layers on the rear side to prevent fecal incontinence leaks. Additionally, there is a long-felt need in the art for a novel underwear or undergarment for men, women, and children that can replace conventional diapers for preventing stains and foul odor caused due to fecal incontinence leaks. Moreover, there is a long-felt need in the art for a novel fecal incontinence brief that helps reduce the stains from fecal incontinence seep through the brief onto clothing. Further, there is a long-felt need in the art of specially designed underwear or undergarment that eliminates the use of wearing adult diapers and includes three sewn layers to cover the buttocks to prevent fecal incontinence leaks. Furthermore, there is a long-felt need in the art for a novel underwear or undergarment that has extended life and is easy to wear. Finally, there is a long-felt need in the art for a fecal incontinence underwear or undergarment that has three layers sewn together on the rear side to form a pad-like structure to absorb fecal incontinence leaks.

The present invention, in one exemplary embodiment, is an anal incontinence leak prevention underwear or undergarment. The underwear or undergarment includes a rear surface, the rear surface has a multi-layered portion disposed thereon which extends from a crotch region along a seam of the rear surface of leg openings to cover the anal region of a wearer of the underwear or undergarment. The multi-layered portion includes an innermost layer made from a moisture-resistant fabric, a middle layer made up of an absorbent material, and an outer layer made of a material consistent with the material used for manufacturing standard underwear or undergarment. The multi-layered portion is adapted to absorb incontinence leaks for more than 6 hours without leakage. The multi-layered portion can have different densities for offering graded protection and comfort.

Referring initially to the drawings, FIG. 1 illustrates a perspective view of the fecal incontinence leak prevention underwear or undergarment in accordance with one embodiment of the present invention. The fecal incontinence leak prevention briefs 100 of the present invention is designed to solve the challenges faced by individuals with fecal incontinence including the risk of leaks and stains on clothing. The fecal incontinence leak prevention briefs 100 is of particular use to the general population of males and females with fecal incontinence, post-partum women, and other similar conditions. The briefs 100 include a multi-layered rear surface 102 adapted to cover the buttock region of a wearer of the briefs 100. Front portion/surface 101 of the undergarment 100 is adapted to cover a frontal portion of a wearer, the rear surface 102 has a multi-layered portion 104 which is made sufficiently wide and long enough to cover the anal region and surrounding area for preventing leakage, and soiling of clothing. The multi-layered portion 104 is also referred to as the multi-layered anal region cover in the present disclosure.

The multi-layered portion 104 extends from a crotch region 106 along seam 108 of the rear surface 102 of the leg openings 110, 112. The multi-layered anal region cover 104 has a first side 114 that extends away from the leg opening 110 and a second side 116 that extends away from the leg opening 112. The first side 114 and the second side 116 meet at a common point 118 to form the closed multi-layered portion 104. The portion 104 covers the anal region up to the cleft of a user, thereby providing effective absorption of incontinence leakage.

The multi-layered portion 104 is flexible and is made of a plurality of layers different from fabrics. The multi-layered portion 104 functions like a pad but provides flexibility, thereby enhancing both the confidence and comfort of the wearer.

Figure 2:
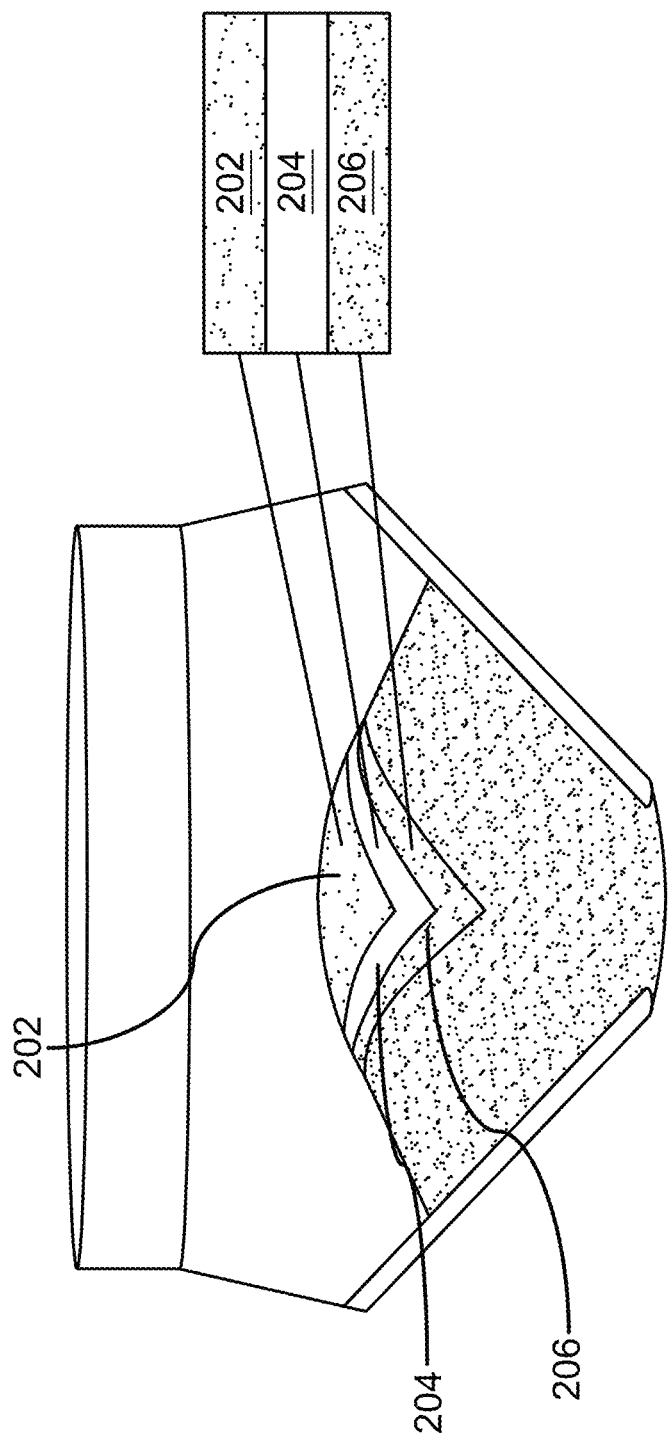
FIG. 2 illustrates a sectional view of the rear surface of the fecal incontinence leak prevention brief of the present invention showing different layers of the multi-layered portion in accordance with the disclosed structure.

FIG. 2 illustrates a sectional view of the rear surface of the fecal incontinence leak prevention brief of the present invention showing different layers of the multi-layered portion in accordance with the disclosed structure. As illustrated, the innermost layer 202 is made from a moisture-resistant fabric, similar to materials used in raincoats and umbrellas. The layer 202 prevents any moisture from leaking out and staining outer clothing. Further, the layer 202 is water-resistant, and traps moisture within the briefs, providing a shield against external leakage.

A middle layer 204 is made up of an absorbent material like terrycloth towel material. The middle layer 204 functions as a buffer, absorbing and isolating moisture away from the skin of the wearer. The middle layer 204 also adds a layer of softness, contributing to the overall comfort of the briefs. An outer layer 206 is made of the same material used for manufacturing the briefs/underwear or undergarments. The outer layer 206 is preferably made of cotton (i.e., fabric) and has the same color as the underwear or undergarment.

All three layers 202, 204, 206 are of similar size and are sewn together to the rear portion of the underwear or undergarment. The three layers 202, 204, 206 provide a pad-like structure that offers comprehensive protection against leaks. The triple-layer construction also contributes to the longevity of the underwear or undergarment as the underwear or undergarment can withstand more wear and tear than single-layered briefs/underwear or undergarment.

The multi-layered portion 104 formed of the layers 202, 204, 206 can have a thickness in the range from about three times to five times the thickness of the material of the underwear or undergarment. Further, depending on the design of the underwear or undergarment 100, the design and shape of the multi-layered portion 104 can be adjusted.

Figure 3:
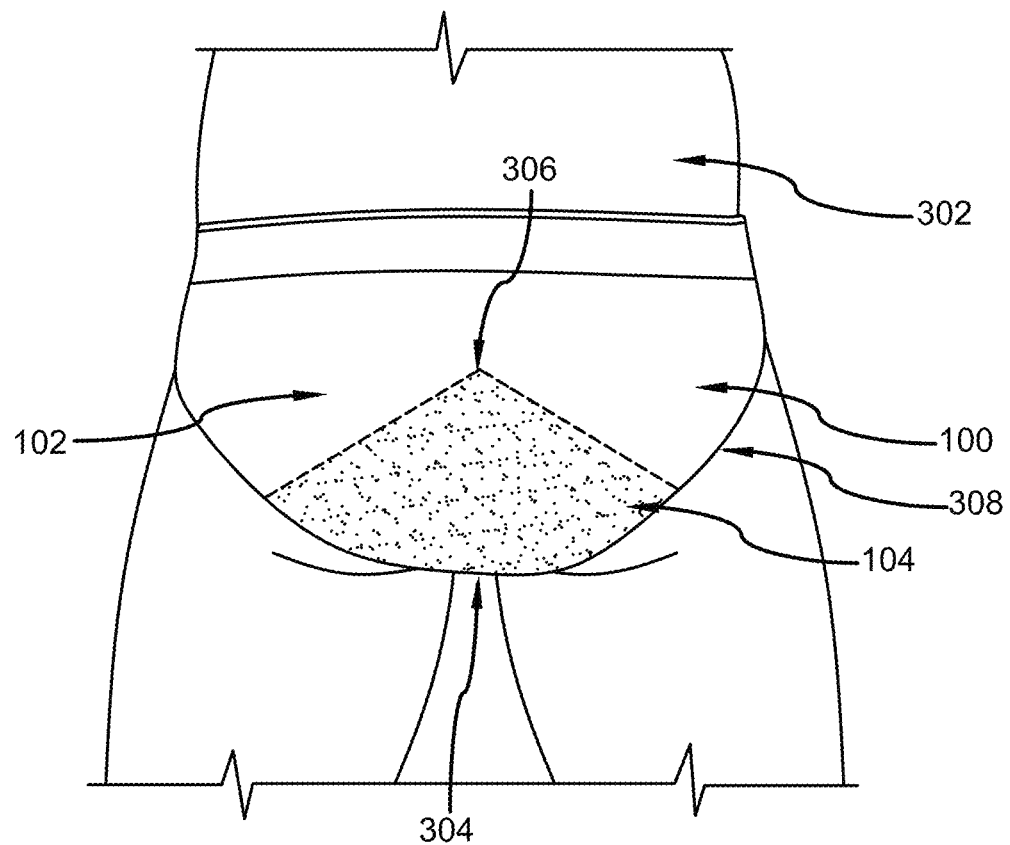
FIG. 3 illustrates a perspective view showing a user wearing the triple-layer construction underwear or undergarment in accordance with one embodiment of the present invention.

FIG. 3 illustrates a perspective view showing a user wearing the triple-layer construction underwear or undergarment in accordance with one embodiment of the present invention. As illustrated, the user 302 wears the underwear or undergarment 100 like a conventional underwear or undergarment and the multi-layered portion 104 covers the anal region 304 up to the cleft 306 and a portion of buttocks 308 of the user 302. The multi-layered portion 104 forms a flexible pad-like structure and can absorb incontinence leaks for more than 6 hours without any leakage.

Figure 4:
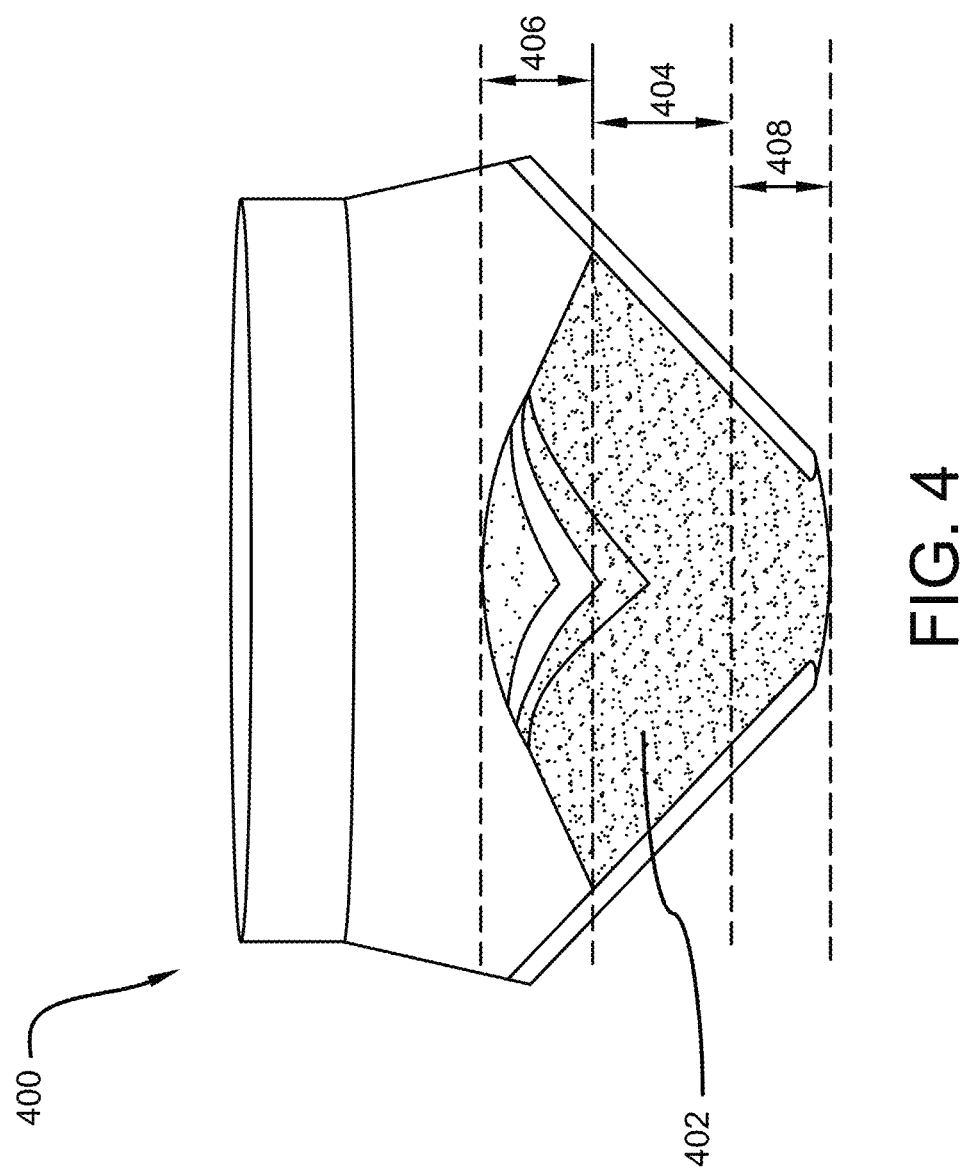
FIG. 4 illustrates a perspective view of another embodiment of the fecal incontinence leak prevention insulating underwear or undergarment of the present invention in accordance with the disclosed structure.

FIG. 4 illustrates a perspective view of another embodiment of the fecal incontinence leak prevention insulating underwear or undergarment of the present invention in accordance with the disclosed structure. In the present embodiment, the multi-layered portion 402 of the undergarment 400 has different thickness along different sections or layers thereof. The middle 404 has the highest density and is used for absorbing the fecal leaks. The top section or layer 406 and the bottom section or layer 408 can have the same density which is from about 40% to about 60% of the density of the middle section or layer 404.

In different embodiments, the multi-layered portion of the underwear or undergarment can cover from about 40% to about 60% of the region of the rear portion of the underwear or undergarment and can also be a part of disposable underwear or undergarment, panty, and more.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "fecal incontinence leak prevention underwear or undergarment", "fecal incontinence leak prevention briefs", "triple-layer construction underwear or undergarment", "fecal incontinence leak prevention insulating underwear or undergarment", and "underwear or undergarment" are interchangeable and refer to the fecal incontinence leak prevention insulating undergarment 100, 400 of the present invention.

Notwithstanding the foregoing, the fecal incontinence leak prevention insulating undergarment 100, 400 of the present invention can be of any suitable size and configuration as is known in the art without affecting the overall concept of the invention, provided that it accomplishes the above-stated objectives. One of ordinary skill in the art will appreciate that the fecal incontinence leak prevention insulating undergarment 100, 400 as shown in the FIGS. are for illustrative purposes only, and that many other sizes and shapes of the fecal incontinence leak prevention insulating undergarment 100, 400 are well within the scope of the present disclosure. Although the dimensions of the fecal incontinence leak prevention insulating undergarment 100, 400 are important design parameters for user convenience, the fecal incontinence leak prevention insulating undergarment 100, 400 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A fecal incontinence leak prevention brief comprising:
   an undergarment comprising:
      a front portion; and
      a flexible multi-layered rear portion;
   wherein said flexible multi-layered rear portion extends from a crotch region of the undergarment and along a seam of rear surfaces of first and second leg openings of the undergarment, and is configured to cover an anal region and surrounding buttock region of a wearer of said undergarment;
   wherein said front portion is configured to cover a frontal region of the wearer of said undergarment;
   wherein said flexible multi-layered rear portion comprises a first side extending away from the first leg opening and a second side extending away from the second leg opening;
   wherein said flexible multi-layered rear portion comprises a first layer including a water-resistant material, a second layer including an absorbent material, and a third layer including a fabric material;
   wherein said second layer absorbs moisture and isolates the moisture away from the skin of the wearer;
   wherein said first layer, said second layer, and said third layer have the same size;
   wherein said first layer, said second layer, and said third layer are sewn together forming said flexible multi-layered rear portion of said undergarment;
   further wherein said first side and said second side meet at a rear common middle point to form said flexible multi-layered rear portion.

2. The fecal incontinence leak prevention brief of claim 1, wherein said flexible multi-layered rear portion covers a majority of a rear seat area of said undergarment.

3. The fecal incontinence leak prevention brief of claim 2, wherein said fabric material of said third layer is the same as a fabric material of said undergarment.

4. The fecal incontinence leak prevention brief of claim 3, wherein said fabric material of said third layer is cotton.

5. A fecal incontinence leak prevention brief comprising:
   an undergarment comprising:
   a front portion; and
   a flexible multi-layered rear portion;
   wherein said flexible multi-layered rear portion extends from a crotch region of the undergarment and along a seam of rear surfaces of first and second leg openings of the undergarment, and is configured to cover an anal region and surrounding buttock region of a wearer of said undergarment;
   wherein said front portion is configured to cover a frontal region of the wearer of said undergarment;
   wherein said flexible multi-layered rear portion comprises a first side extending away from the first leg opening and a second side extending away from the second leg opening;
   wherein said first side and said second side meet at a rear common middle point to form said flexible multi-layered rear portion;
   wherein said flexible multi-layered rear portion comprises a first layer including a water-resistant material, a second layer including an absorbent material, and a third layer including a fabric material; and
   further wherein said rear common middle point is configured to extend to a position above a cleft area of the wearer of said undergarment.

6. The fecal incontinence leak prevention brief of claim 5, said flexible multi-layered rear portion covering a majority of a rear seat area of said undergarment.

7. The fecal incontinence leak prevention brief of claim 5, wherein said second layer absorbs moisture and isolates the moisture away from the skin of the wearer.

8. The fecal incontinence leak prevention brief of claim 5, wherein said first layer, said second layer, and said third layer have the same size.

9. The fecal incontinence leak prevention brief of claim 5, wherein said first layer, said second layer, and said third layer are sewn together forming said flexible multi-layered rear portion of said undergarment.

10. The fecal incontinence leak prevention brief of claim 5, wherein said fabric material of said third layer is the same as a fabric material of said undergarment.

11. The fecal incontinence leak prevention brief of claim 10, wherein said fabric material of said third layer is cotton.

12. A fecal incontinence leak prevention brief comprising:
    an undergarment comprising:
    a front portion; and
    a flexible multi-layered rear portion;
    wherein said flexible multi-layered rear portion extends from a crotch region of the undergarment and along a seam of rear surfaces of first and second leg openings of the undergarment, and is configured to cover an anal region and surrounding buttock region of a wearer of said undergarment;
    wherein said front portion is configured to cover a frontal region of the wearer of said undergarment;
    wherein said flexible multi-layered rear portion comprises a first side extending away from the first leg opening and a second side extending away from the second leg opening;
    wherein said first side and said second side meet at a rear common middle point to form said flexible multi-layered rear portion;
    wherein said flexible multi-layered rear portion comprises a first layer including a water-resistant material, a second layer including an absorbent material, and a third layer including a fabric material;
    wherein said first layer has a first thickness, said second layer has a second thickness, and said third layer has a third thickness;
    wherein said first thickness is the same as said third thickness; and
    further wherein said first thickness and said third thickness are each 40% to 60% of said second thickness.

13. The fecal incontinence leak prevention brief of claim 12, said flexible multi-layered rear portion covering a majority of a rear seat area of said undergarment.

14. The fecal incontinence leak prevention brief of claim 12, wherein said second layer absorbs moisture and isolates the moisture away from the skin of the wearer.

15. The fecal incontinence leak prevention brief of claim 12, wherein said first layer, said second layer, and said third layer have the same size.

16. The fecal incontinence leak prevention brief of claim 12, wherein said first layer, said second layer, and said third layer are sewn together forming said flexible multi-layered rear portion of said undergarment.

\* \* \* \* \*